US012746332B2

(12) United States Patent
Lambert et al.

(10) Patent No.: US 12,746,332 B2
(45) Date of Patent: Sep. 29, 2026

(54) DIFFERENTIAL PRESSURE FLUID DELIVERY SYSTEM

(71) Applicant: BIO HEALTH FRONTIERS, INC., El Dorado Hills, CA (US)

(72) Inventors: Paul Lambert, El Dorado Hills, CA (US); Cesar Perez, El Dorado Hills, CA (US); Carlos Gutierrez, El Dorado Hills, CA (US); Neal De Beer, El Dorado Hills, CA (US); Travis F. Schraeder, El Dorado Hills, CA (US)

(73) Assignee: BIO HEALTH FRONTIERS, INC., El Dorado Hills, CA (US)

( * ) Notice: Subject to any disclaimer, the term of this patent is extended or adjusted under 35 U.S.C. 154(b) by 926 days.

(21) Appl. No.: 17/774,100

(22) PCT Filed: Nov. 6, 2020

(86) PCT No.: PCT/US2020/059278

§ 371 (c)(1),
(2) Date: May 3, 2022

(87) PCT Pub. No.: WO2021/092284

PCT Pub. Date: May 14, 2021

(65) Prior Publication Data

US 2022/0387708 A1 Dec. 8, 2022
US 2023/0109668 A9 Apr. 6, 2023

Related U.S. Application Data

(60) Provisional application No. 62/933,223, filed on Nov. 8, 2019.

(51) Int. Cl.

| | |
|---|---|
| *A61M 5/168* | (2006.01) |
| *A61M 5/145* | (2006.01) |

(52) U.S. Cl.

CPC ........ *A61M 5/16854* (2013.01); *A61M 5/145* (2013.01); *A61M 5/16881* (2013.01);

(Continued)

(58) Field of Classification Search

CPC .............. A61M 5/145; A61M 5/16854; A61M 4/14526; A61M 2005/14513; A61M 2205/3379; A61M 5/14526; A61M 5/155

See application file for complete search history.

(56) References Cited

U.S. PATENT DOCUMENTS 5,354,273 A * 10/1994 Hagen ............... A61M 5/16854 604/67
6,302,653 B1 * 10/2001 Bryant .................... F04B 51/00 417/63

(Continued)

FOREIGN PATENT DOCUMENTS

BR 112020016503 A2 * 12/2020 ............ A61M 37/00
EP 3278825 A2 2/2018

(Continued)

OTHER PUBLICATIONS

International Search Report and Written Opinion for International Patent Application No. PCT/US2020/059278 (Pub No. WO 2021/092284) mailed Feb. 25, 2021 (14 pages).

*Primary Examiner* — Courtney Fredrickson
*Assistant Examiner* — Kayla M. Turkowski
(74) *Attorney, Agent, or Firm* — Jones Day

(57) ABSTRACT

A system for delivering a medicinal fluid to a patient includes a variable volume pressure delivery chamber, a variable volume medication chamber, an optional medication reservoir, a movable delivery element, a fixed reference volume chamber, a pressure source, and a control subsystem. The variable volume pressure delivery chamber is configured to store pressure controllably. The variable volume medication chamber is fluidically isolated from the (Continued)

pressure delivery chamber and is configured to store medicinal fluid. The movable delivery element is disposed between the medication chamber and the pressure delivery chamber. The pressure source is coupled to the pressure delivery chamber. The control system is configured to selectively cause the pressure source to deliver pressure to the pressure delivery chamber causing the movable delivery element to apply pressure to the medicinal fluid in the medication chamber thereby causing the medicinal fluid to exit the medication chamber at an outlet along the fluid communication path to the patient.

31 Claims, 4 Drawing Sheets

(52) U.S. Cl.
CPC ............... *A61M 2205/3334* (2013.01); *A61M 2205/502* (2013.01)

(56) References Cited

U.S. PATENT DOCUMENTS

| | | | | |
|---|---|---|---|---|
| 7,654,127 | B2 | 2/2010 | Krulevitch et al. | |
| 2007/0264130 | A1* | 11/2007 | Mallett | G01F 1/34 73/744 |
| 2008/0139996 | A1 | 6/2008 | Bowman et al. | |
| 2008/0154187 | A1* | 6/2008 | Krulevitch | A61M 5/14526 604/48 |
| 2010/0262078 | A1 | 10/2010 | Blomquist | |
| 2011/0066131 | A1* | 3/2011 | Cabiri | A61M 5/14248 604/411 |
| 2012/0265174 | A1* | 10/2012 | Gray | A61M 5/14593 604/891.1 |
| 2013/0184640 | A1* | 7/2013 | Li | A61M 5/172 604/67 |
| 2013/0184676 | A1* | 7/2013 | Kamen | A61M 5/1458 604/152 |
| 2014/0039392 | A1* | 2/2014 | Geipel | A61M 5/365 604/152 |
| 2014/0276415 | A1* | 9/2014 | Davis | A61M 39/20 604/150 |
| 2015/0328399 | A1* | 11/2015 | Heitmeier | A61M 5/14593 604/67 |
| 2015/0335817 | A1* | 11/2015 | Lambert | A61M 5/14526 604/153 |
| 2016/0023233 | A1* | 1/2016 | Hayashi | B05C 5/0225 222/544 |
| 2016/0278899 | A1* | 9/2016 | Heller | A61K 31/198 |
| 2016/0346485 | A1* | 12/2016 | Mohr | B01D 19/0031 |
| 2017/0089746 | A1* | 3/2017 | Rossi | A61M 1/3666 |
| 2017/0290971 | A1* | 10/2017 | Hedmann | A61M 60/113 |
| 2019/0151569 | A1* | 5/2019 | Fangrow | A61M 5/14546 |
| 2019/0275241 | A1* | 9/2019 | Ring | A61M 5/14248 |
| 2020/0164155 | A1* | 5/2020 | Mojarrad | A61M 5/3202 |
| 2022/0273876 | A1* | 9/2022 | Menz | A61M 5/20 |

FOREIGN PATENT DOCUMENTS

| | | |
|---|---|---|
| WO | WO 2013075109 A2 | 5/2013 |
| WO | WO 2017123703 A2 | 7/2017 |

* cited by examiner

DIFFERENTIAL PRESSURE FLUID DELIVERY SYSTEM

RELATED APPLICATION

The current application is a U.S. National Stage filing under 35 U.S.C. § 371 of International Application No. PCT/US2020/059278, filed on Nov. 6, 2020, which claims priority to U.S. Patent Application No. 62/933,233, filed on Nov. 8, 2019, the contents of both of which are hereby fully incorporated by reference.

FIELD

The disclosure relates generally to medicament delivery devices and, in particular, to a closed-loop infusion pump apparatus that can be reusable or partly reusable which utilizes differential pressure measurements.

BACKGROUND

In many infusion therapy applications, a medicinal fluid is required to be administered to the patient at a certain fluid flow rate and fluid volume to be optimized therapeutically. For example, in some applications, if the medicinal fluid is infused too slowly, the intended therapeutic effect may be diminished or totally non-existent. In other applications, infusion of a medicinal fluid into the body at too high a rate can create unintended side effects. Thus, in a number of infusion therapy applications it is important for the user to be able to quickly and accurately determine the rate of fluid flow through an infusion system, so that the flowrate can be monitored and adjusted as needed.

SUMMARY

In a first aspect, a system for delivering a medicinal fluid to a patient includes a variable volume pressure delivery chamber, a variable volume medication chamber, a movable delivery element, a pressure source, and a control sub-system. The variable volume pressure delivery chamber is configured to store pressure controllably. The variable volume medication chamber is fluidically isolated from the pressure delivery chamber and is configured to store medicinal fluid and having an outlet forming a fluid communication path to the patient. The movable delivery element is disposed between the medication chamber and the pressure delivery chamber. The pressure source is coupled (either directly or indirectly) to the pressure delivery chamber. The control system is configured to selectively cause the pressure source to deliver pressure to the pressure delivery chamber causing the movable delivery element to apply pressure to the medicinal fluid in the medication chamber thereby causing the medicinal fluid to exit the medication chamber at the outlet along the fluid communication path to the patient.

The movable delivery element can take many forms. For example, the movable delivery element can be at least partially movable within at least a portion of the medication chamber. In addition or in the alternative, the movable delivery element can be at least partially deformable. The movable delivery element can include one or more of a gasket, a syringe plunger, an elastomeric element, a bellows element with collapsible sides, a membrane, or a balloon.

A volume of the pressure delivery chamber can vary based on an amount of pressure delivered by the pressure source or an amount of pressure within the medication chamber.

The medication chamber can include at least a portion of a medication container such as a syringe (e.g., pre-filled syringe, etc.). In some cases, the medication container can be detachably secured to the medication chamber (and forming part of the medication chamber when secured).

A valve manifold can be disposed between the pressure source and the pressure delivery chamber for selectively delivering (i.e., increasing pressure and/or decreasing pressure, etc.) pressure from the pressure source to the pressure delivery chamber in response to receiving a signal from the control sub-system.

A position sensor can be coupled or adjacent to the medication chamber which is in communication with the control sub-system. The position sensor can generate data indicative of a volume of medicinal fluid within the medication chamber. The control sub-system can calculate a flow rate and/or volume of the medicinal fluid exiting the outlet of the medication chamber based on the data generated by the position sensor.

A flow sensor can be coupled or adjacent to the medication chamber which is in communication with the control sub-system. The flow sensor can generate data indicative of a rate of flow of medicinal fluid exiting the medication chamber. The control sub-system can calculate a flow rate and/or volume of the medicinal fluid exiting the outlet of the medication chamber based on the data generated by the flow sensor.

A mass sensor can be coupled or adjacent to the medication chamber which is in communication with the control sub-system. The mass sensor can generate data indicative of a mass of medicinal fluid within the medication chamber. The control sub-system calculates a flow rate and/or volume of the medicinal fluid exiting the outlet of the medication chamber based on the data generated by the mass sensor.

A medication chamber pressure sensor can be coupled or adjacent to the medication chamber which is in communication with the control sub-system. The medication chamber pressure sensor can generate data indicative a level of pressure in the medication chamber. The control sub-system can calculate a volume and/or a flow rate of the medicinal fluid exiting the outlet of the medication chamber based on the data generated by the medication chamber pressure sensor.

A pressure delivery chamber pressure sensor can be coupled to or adjacent to the pressure delivery chamber which is in communication with the control sub-system and can generate a first pressure value characterizing a level of pressure within a pressure delivery chamber. A reference pressure chamber pressure sensor can be coupled to or adjacent to the reference pressure chamber which is in communication with the control sub-system and can generate a second pressure value characterizing a level of pressure within the reference pressure chamber. The control sub-system can calculate an amount of medical fluid amount within the medication chamber based on a differential pressure measurement using the first pressure values and the second pressure value. In some variations, the control sub-subsystem can further calculate occlusions within the fluid communication path using the first pressure values and the second pressure values.

In some variations, a medication chamber pressure sensor can be coupled to or adjacent to the medication chamber which is in communication with the control sub-system and which generates a pressure value characterizing a level of pressure within the medication chamber. In such variations, the control sub-system can calculate an amount of medical fluid amount within the medication chamber based on a differential pressure measurement using the first pressure values and the second pressure value.

The pressure source can take various forms including an elastomeric balloon, a pressurized chamber, an electromechanical air pump, a piezoelectric air pump, and the like.

The fluid delivery system can be configured to couple or otherwise include a medication reservoir coupled to the medication chamber holding additional medicinal fluid. The control sub-system, in turn, can be configured to automatically extract the additional medicinal fluid from the medication reservoir to the medication chamber.

A bubble detection sensor can be coupled to or adjacent to the medication chamber which is in communication with the control sub-system which is configured to identify bubbles within the medicinal fluid. A bubble elimination system can be coupled to or adjacent to the medication chamber which is in communication with the control sub-system which is configured to selectively remove bubbles within the medicinal fluid identified by the bubble detection sensor.

An occlusion detection sensor can be coupled to or adjacent to the medication chamber which is in communication with the control sub-system configured to identify an occlusion within the fluid communication path.

A user interface can be included which has a display and at least one input element configured to alter a parameter associated with delivery of the medicinal fluid to the patient.

The form factor of the fluid delivery system can vary depending on the application. In one implementation, the fluid delivery system is handheld such that a housing can be held in one hand by a user and the at least one input element can be activated by the other hand of the user. In some variations (including handheld and larger variations), the housing can encapsulate each of the pressure delivery chamber, the medication chamber, the movable delivery element, the pressure source, and the control sub-system. Other components described herein can also be within the housing unless otherwise specified. The form factors may include pole mounted, ambulatory or wearable devices.

The control sub-system can include or otherwise connect to a communications interface configured to bi-directionally exchange data over a communications network with a remote computing device (e.g., cloud system, a mobile phone, another medical device, etc.) associated with delivery of the medicinal fluid.

In an interrelated aspect, medicinal fluid is delivered to a patient using a fluid delivery system having a pressure delivery chamber, a medication chamber, and a reference chamber. With such an arrangement, pressure is monitored within the pressure delivery chamber, the medication chamber housing the medicinal fluid or a reference chamber having a known pressure level. Thereafter, a pressure source coupled to the pressure delivery chamber is selectively activated to increase or decrease a level of pressure within the pressure delivery chamber based on the respective monitoring. The increase in pressure in the pressure delivery chamber causes a movable delivery element between the pressure delivery chamber and the medication chamber to apply pressure to the medication chamber thereby causing medicinal fluid to be delivered along a fluid communication path to the patient.

The details of one or more variations of the subject matter described herein are set forth in the accompanying drawings and the description below. Other features and advantages of the subject matter described herein will be apparent from the description and drawings, and from the claims.

and

Figure 1:
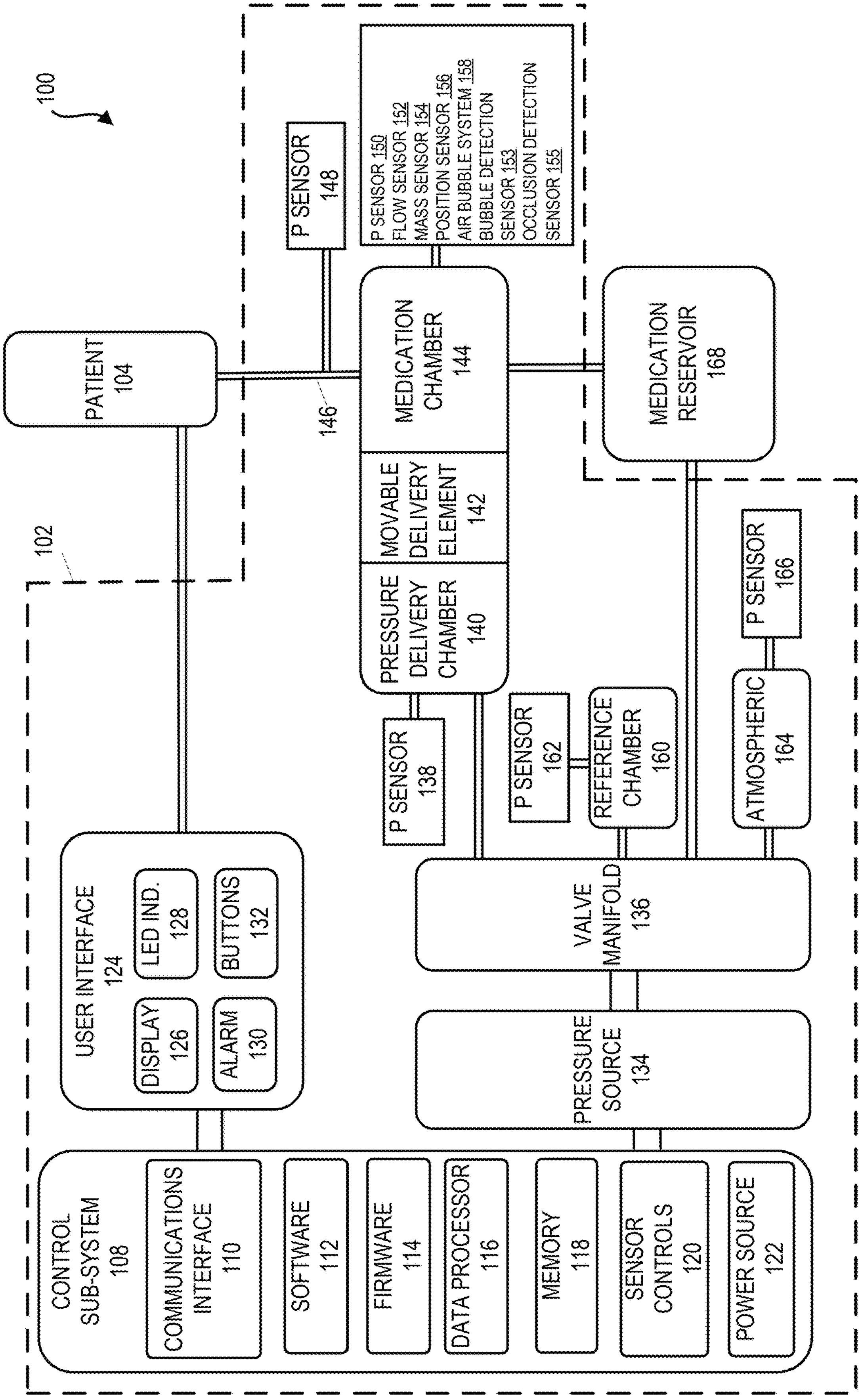
FIG. 1 is a block diagram of an infusion pump system for delivering a medicine or drug to a patient.
Figure 4:
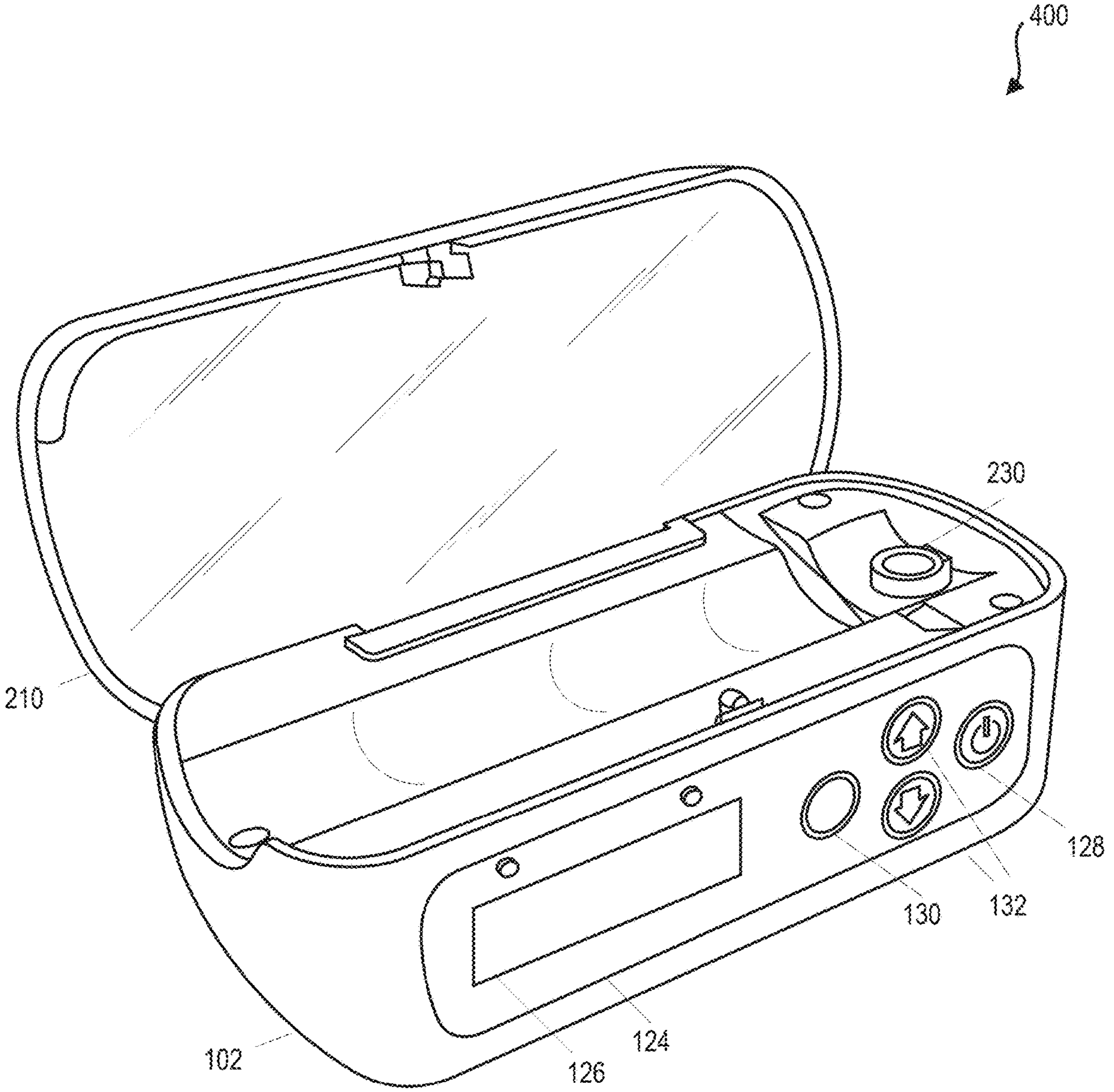

FIG. 4 is a third diagram illustrating an infusion pump system as in FIG. 1.

Like reference symbols in the various drawings indicate like elements.

DETAILED DESCRIPTION

The current subject matter is directed to advanced fluid delivery devices for a variety of applications including the delivery of medicinal fluid to a patient. While the structure and description below describes a particular medical application, it will be appreciated that the current subject matter can be applied to other fluid delivery applications including microfluidics and the like.

FIG. 1 is block diagram 100 illustrating components that form part of a fluid delivery system 102 which can be configured to provide medicinal fluid to a patient 104 over a fluid communication path 146. The fluid delivery system 102 can include a control sub-system 108 which is in electrical communication with various other components as described below. The control sub-system 108 can include a communications interface 110 which allows for bi-directional transfer of data to a remote computing device such as a cloud communication server, a proximate computing device (e.g., via a BLUETOOTH connection, etc.) and/or to a wireless network (e.g., cellular, WiFi, etc.). The control sub-subsystem 108 can include software which can be loaded into memory 118 for execution by a processor 116 (e.g., a microprocessor, a multi-core CPU, multi-core GPU, system on a chip (SoC), etc.). The memory can be used to implement programming instructions received either via the communications interface 110 or, in some variations, a user interface 124. In some cases, various functionalities of the control sub-system 110 can be embedded in firmware 114. In some variations, the control sub-system includes sensor controls 120 which provide communication interfaces with a plurality of on-board sensors forming part of the fluid delivery system 102. Software 112 and/or the firmware 114 can be executed by the processor 116 to cause the sensor controls 120 to, in turn, perform a particular action and/or to receive measurement data from such sensors. Further, in some variations, the control sub-system 108 can include a power source 122 such as battery and, optionally, in some variations, on-board recharging circuitry. It will be appreciated that certain aspects of the control sub-system 108 such as the power source 122 can be external to the control sub-system 108 but within a housing forming part of the fluid delivery system 102 or, alternatively, components such as the power source 122 can be external and separate from the fluid delivery system 102 (e.g., a hard-wired electricity connection, etc.).

The user interface 124 can comprise an electronic visual display 126 to convey certain information relating to the delivery of fluid. In some cases, the electronic visual display 126 is a touch-screen interface allowing for selection of displayed graphical user interface elements associated with the operation of the fluid delivery system 102. In other variations, there can be dedicated physical elements such as a LED indicator 128 which can, convey a status of the fluid delivery system 102 such as on/off, operating, error, etc. An alarm element 130 can display a visual indicator associated with the operation of the fluid delivery system 102. In some cases, the alarm element 130 can convey an audio signal and in other variations the alarm can convey both a visual indicator and convey an audio signal. Various physical buttons 132 can also be provided to allow a user (such as the patient 104 when medicinal fluid is self-administered, etc.) to obtain information associated with the operation and control of the fluid delivery system 102.

One of the major functions of the control sub-system 108 is to control and drive a pressure source 134 in combination with a valve manifold 136 which can cause pressure originating from the pressure source 134 to be selectively delivered to other components within the fluid delivery system. The pressure source 134 can be an elastomeric device that is pressurized with water or another impelling fluid, but the impelling fluid is fluidly isolated from the medicinal fluid contained within a medication chamber 144. In other variations, the pressure source 134 is an air pump (e.g., a piezoelectric air pump, etc.) that includes an air chamber adapted to be pressurized with air. The pressure source 134 can be utilized multiple times. The pressure source 134 can serve as an engine that propels the medicinal fluid out of a separate, fluidly isolated medication chamber 144 so that the medicinal fluid does not contact the pressure delivery chamber 140 but instead flows directly into the patient propelled by the pressure in the pressure delivery chamber 140 (which reduces costs of any single use components/disposables and/or the medication chamber 144).

The valve manifold 136 can be an electro-mechanical valve system that is controlled by the control sub-system 108 (either integrated into a single unit as illustrated or distributed across multiple electro-mechanical valves). Each individual valve, can for example, be a solenoid valve. The pressure source 134 in combination with the valve manifold 136 can cause a variable volume pressure delivery chamber 140 to be selectively pressurized. As will be described in further detail below, the addition of pressurized fluid (e.g., air or other gas, fluid, etc.) from the pressure source 134 can cause the pressure delivery chamber 140 to apply pressure to a medication chamber 144. The medication chamber 144 can comprise a dedicated container for housing a fluid such as a medicinal fluid or, in other variations, the medication chamber 144 can have a shape and size to receive an external medication container such as a pre-filled syringe (without a plunger, etc.) or vial. Because the fluid delivery system 102 can use pre-filled syringes and vials there is no need to transfer the drug or medicine from a manufacturing format container to a subsequent delivery reservoir. For example, the situation requiring transfer of a drug from a special container, which lacks a compatible connector, into a syringe or other delivery container designed to interconnect with the rest of the pump can be obviated. Such an arrangement provides an important simplification in the clinical setting which also reduces issues inherent to the manipulation of the drug in a non-sterile environment, such as potential leakage, drug contamination or exposure. For example, eliminating medicinal fluid transfers reduces risks of exposure for reactive pharmaceuticals such as those involved in chemotherapy or similar chemically abrasive drugs.

A movable delivery element 142 can be disposed between the pressure delivery chamber 140 and the medication chamber 144 which fluidically isolates (thus preserving sterility, etc.) such chambers 140, 144 while, at the same time, imparting pressure on the medication chamber 144 which, in turn, causes fluid disposed therein to be delivered to the patient 104 along a fluid communication path 146. The movable delivery element 142 can take different forms including an elastomeric membrane which is at least partially fixed and has movable and/or deformable elements, an expandable balloon (which expands into the medication chamber 144 when pressure is delivered to the pressure delivery chamber 140), a plunger-like element, a gasket, a bellows element with collapsible sides and the like. Isolating fluidic contact between the medication chamber 144 and the pressure source 134/pressure delivery chamber eliminates any drug incompatibility issue or leaching issue with the medicinal fluid and the impelling fluid and the medicine and the first chamber, respectively, because the medicinal fluid does not come into contact with the impelling fluid or gas.

In some variations, the medication chamber 144 can be selectively coupled to a medication reservoir 168. The medication reservoir 168 can hold additional medicinal fluid (or the first fill for the patient) for delivery to the patient via the medication chamber 144 and the fluid communication path 146. The medication reservoir 168 can take various forms including a pre-filled syringe, a vial, a bag and the like. In some cases, the medication reservoir 168 is selectively attachable to the fluid delivery system 102 for example, by a Luer lock or other physical connection system/tubing set. When the medication chamber 144 is empty or low on fluid, pressure applied from the pressure delivery chamber 140 can cause a suction effect when an opening between the medication reservoir 168 and the medication chamber 144 is open thereby drawing fluid from the medication reservoir 168 into the medication chamber 144.

The fluid delivery system 102 can optionally include a fixed volume reference chamber 160 and/or an atmospheric port 164 each of which may have a corresponding pressure sensor 162, 166. These pressure sensors 162, 166 can generate pressure measurements which are then provided to the control sub-system 108 can take various forms including, for example absolute pressures, gauge pressures, or differential pressures between different pressure sensors. Furthermore, the pressure delivery chamber 140 can also include a dedicated pressure sensor 138. The medication chamber 144 can also include an additional pressure sensor 150. In some cases, an additional pressure sensor 148 is present along the fluid communication path 146. The outputs of two or more of the pressure sensors 138, 148, 150, 162, and 166 can be used by the control sub-system 108 to determine one or more parameters relating to delivery of fluid to the patient 104 including, for example, algorithms to derive from pressure measurements, flow rate and/or volume of fluid remaining, etc. Pressure sensor 148 at the patient 104 is helpful to monitor the pressure of the medicinal fluid that is applied to the patient 104 which is a direct way to control the pressure profile. The outputs of pressure sensor 138 and pressure sensor 162 provide an indirect way to control the volume without using other sensors including pressure sensor 148. The control sub-system 108 by way of the data processor 116 can cause the pressure source 134 in concert with the valve manifold 136 to selectively deliver pressurized air/fluid to the pressure delivery chamber 140 to effect a desired output (e.g., flow rate, volume, refill, etc.) of fluid in the medication chamber 144.

In some variations, there can be one or more ancillary sensors coupled to the medication chamber 144 and in communication with the control sub-system 108. For example, a dedicated flow sensor 152 can monitor a rate of flow of fluid (e.g., medicinal fluid) exiting the medication chamber 144 and/or entering the medication chamber 144 from the medication reservoir. A mass sensor 154 can be used to determine a mass and/or density of fluid in the medication chamber 144 which, in turn, can be used by the sub-control sub-system 108 to determine a change of volume of fluid within the medication chamber 144 which can be used to determine flow rate and/or volume, etc. A position sensor 168 can be utilized which can identify a position of one or more of the movable delivery element 142 within the medication chamber 144, a level of fluid within the medication chamber 144 and/or a position of a movable element such as a pre-filled syringe plunger forming part of the medication chamber 144. Still further, an air bubble system 158 can be provided that identifies whether there are any bubbles within medication chamber 144 but at least within communication path 146 which, in turn, could pose problems for the patient 104. In such cases, a priming routine or other air bubble removal technique may be initiated by the control sub-system 108 in concert with the pressure source 134, one or more of the pressure sensors 138, 148, 150, 162, 166, and the valve manifold 136. A bubble detection sensor 153 can be coupled to or adjacent to the medication chamber 144 which is in communication with the control sub-system 108. The bubble detection sensor 153 can be configured to identify bubbles within the medicinal fluid. An occlusion detection sensor 155 can be coupled to or adjacent to the medication chamber 144 which is in communication with the control sub-system 108. The occlusion detector sensor 155 can be configured to identify an occlusion within the fluid communication path.

The control sub-system 108 can generate signals that cause the pressure source 134 in concert with the valve manifold 136 to dispense medicinal fluid out of the medication chamber 144 at a desired steady flow rate, or in a stepped manner (i.e., changing a pressure level at certain intervals for specific periods of time) to deliver a series of discrete medicinal fluid volumes. The operation used often depends on the drug regimen. For instance, diabetes patients usually need a continuous, low "basal" rate of insulin, in addition to high-rate, short-duration "bolus" deliveries before or after meals. In this case, the patient 104 or caregiver can use the user interface 124 to enter at least one parameter for controlling the delivery of the medicinal fluid to the patient 104, corresponding to either a rate of fluid flow, a volume of fluid flow, a time of fluid flow, and/or a duration of fluid flow. With this arrangement, the fluid delivery system 102 can control flow rate and/or volume and/or pressure profiles independently and as such, improve therapy mode control and optimization of clinical benefits.

Figure 2:
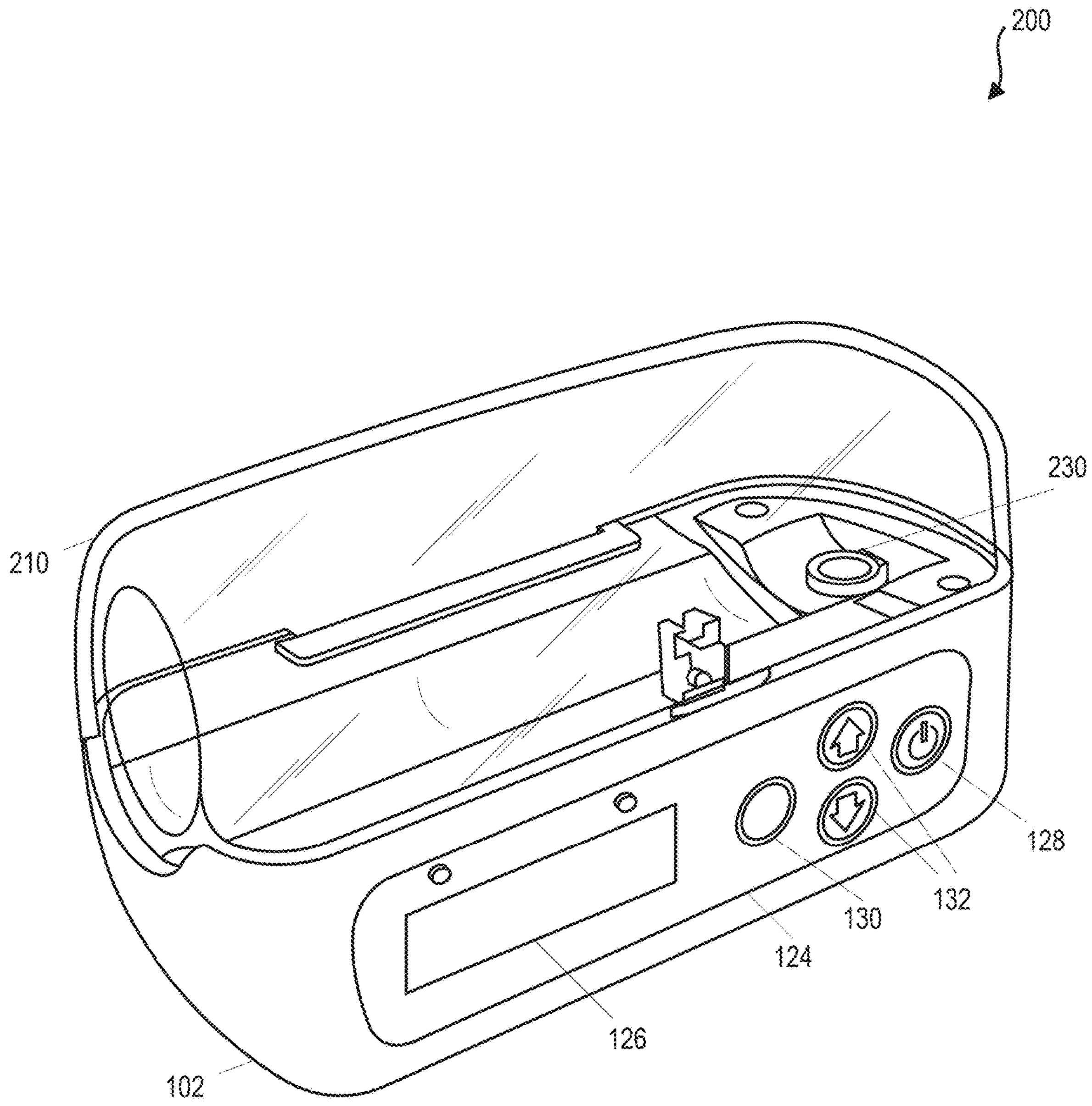
FIG. 2 is a first diagram illustrating an infusion pump system as in FIG. 1.
Figure 3:
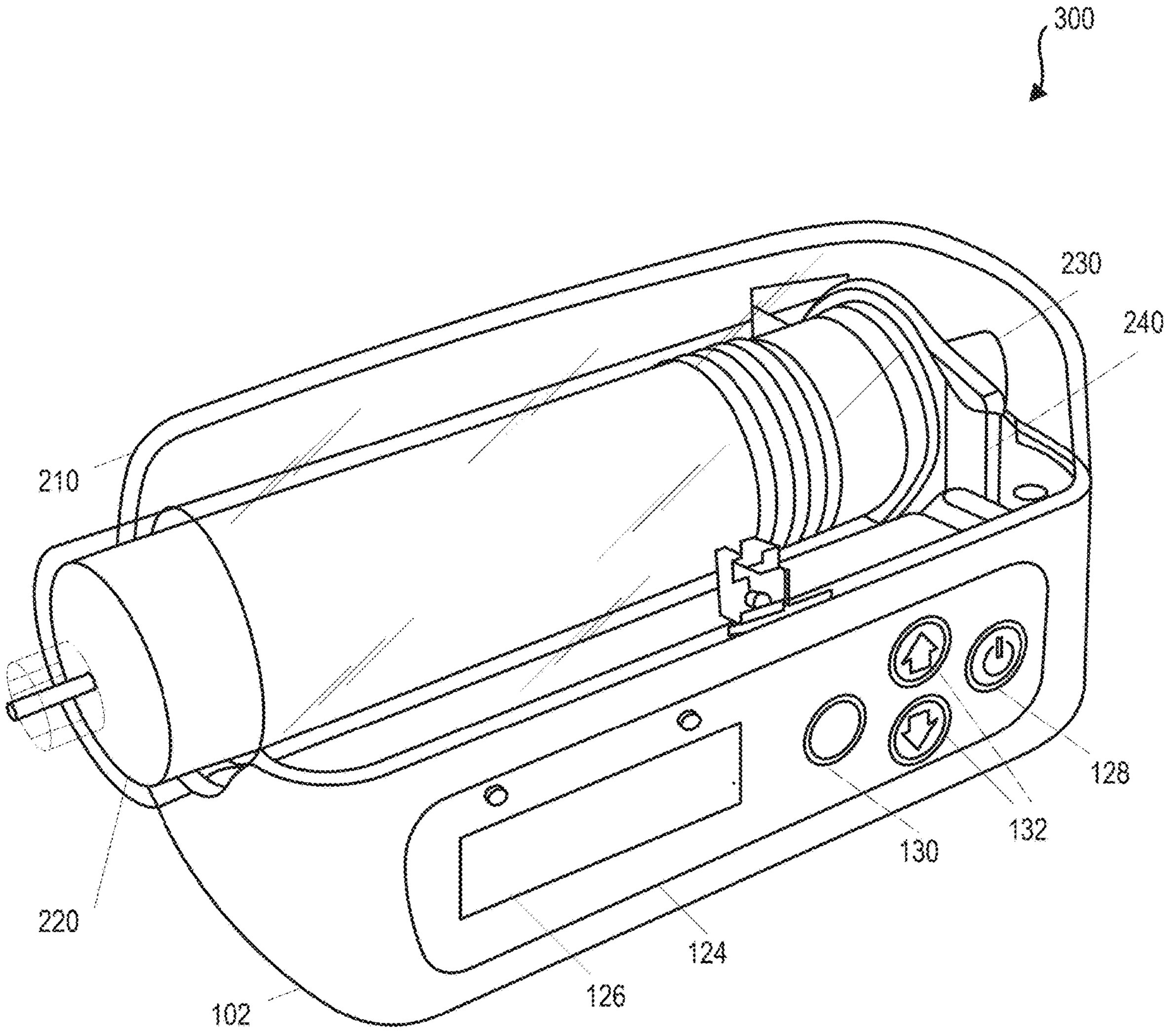
FIG. 3 is a second diagram illustrating an infusion pump system as in FIG. 1.

FIGS. 2-4 are diagrams 200, 300, 400 illustrating one implementation of a hand-held fluid delivery system in which the medication chamber 144 comprises a lid 210 which may be opened so that a container such as a pre-filled syringe 220 can be inserted therein. The pre-filled syringe can, in some variations, be mechanically and fluidically coupled to the fluid delivery system 102 using a mechanical connector 230 (such as a Luer lock compatible with threads on a tip of the pre-filled syringe or a proprietary connector) thus forming part of the medication chamber 144. In other variations, the medical container such as the pre-filled syringe does not form part of the medication chamber 144. For example, with reference to FIG. 3, initially the pre-filled syringe is connected to coupler 240 which is configured to interconnect hermetically with connector 230. When the pre-filled syringe is ready with coupler 240, the lid 210 may be opened so that the pre-filled syringe 220 may be secured to the connector 230 with a leak-proof connection. Further, the lid 210 can then be closed. In some variations, the lid 210 completely covers the pre-filled syringe 220 when closed. In some other variations, the lid 210 may be replaced by a reservoir entirely.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language or firmware. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above in relation to the delivery of medicinal fluid, other applications, modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system for delivering a medicinal fluid to a patient comprising:

a connector configured to receive and secure a detachable, pre-filled syringe, at least a portion of the syringe defining a medication chamber having a variable volume, the medication chamber configured to store medicinal fluid and having an outlet forming a fluid communication path to the patient;

a pressure delivery chamber having a variable volume and configured to store pressure controllably, the pressure delivery chamber being fluidically isolated from the medication chamber;

a movable delivery element disposed between the medication chamber and the pressure delivery chamber, the movable delivery element having a shape and size to fluidically isolate the medication chamber and the pressure delivery chamber;

a pressure source coupled to the pressure delivery chamber, the pressure source comprising an electromechanical air pump that is configured to be utilized multiple times to selectively increase or decrease pressure within the pressure delivery chamber;

a pressure delivery chamber pressure sensor coupled to or adjacent to the pressure delivery chamber and configured to generate a first pressure value;

a reference pressure chamber having a fixed volume and a reference pressure chamber pressure sensor coupled to or adjacent to the reference pressure chamber and configured to generate a second pressure value;

a medication reservoir configured to be coupled to the medication chamber and configured to hold additional medicinal fluid;

a control sub-system configured to send signals to the electromechanical air pump to selectively cause pressure to be delivered from the pressure source to the pressure delivery chamber, causing the movable delivery element to apply pressure to the medicinal fluid in the medication chamber, the application of pressure to the medicinal fluid thereby causing the medicinal fluid to exit the medication chamber at the outlet along the fluid communication path to the patient, the control sub-system being configured to calculate an amount of medicinal fluid within the medication chamber based on a differential pressure measurement using the first pressure value and the second pressure value, the control sub-system being further configured to automatically extract fluid from the medication reservoir and transfer the extracted fluid to the medication chamber; and a handheld housing encapsulating each of the pressure delivery chamber, the movable delivery element, the pressure source, the pressure delivery chamber pressure sensor, the reference pressure chamber, the reference pressure chamber pressure sensor, the medication reservoir, and the control sub-system.

2. The system of claim 1, wherein the movable delivery element is at least partially movable within at least a portion of the medication chamber.

3. The system of claim 1, wherein the movable delivery element is at least partially deformable.

4. The system of claim 1, wherein a volume of the pressure delivery chamber varies based on an amount of pressure delivered by the pressure source or an amount of pressure within the medication chamber.

5. The system of claim 1 further comprising:

a valve manifold disposed between the pressure source and the pressure delivery chamber for selectively delivering pressure from the pressure source to the pressure delivery chamber in response to receiving a signal from the control sub-system.

6. The system of claim 1, wherein the movable delivery element comprises a gasket, a syringe plunger, an elastomeric element, a bellows element, a membrane, or a balloon.

7. The system of claim 1 further comprising a position sensor coupled or adjacent to the medication chamber, the position sensor being in communication with the control sub-system, the position sensor generating data indicative of a volume of medicinal fluid within the medication chamber.

8. The system of claim 7, wherein the control sub-system calculates a flow rate and/or volume of the medicinal fluid exiting the outlet of the medication chamber based on the data generated by the position sensor.

9. The system of claim 1 further comprising a flow sensor coupled or adjacent to the medication chamber, the flow sensor being in communication with the control sub-system, the flow sensor generating data indicative of a rate of flow of medicinal fluid exiting the medication chamber.

10. The system of claim 9, wherein the control sub-system calculates a flow rate and/or volume of the medicinal fluid exiting the outlet of the medication chamber based on the data generated by the flow sensor.

11. The system of claim 1 further comprising a mass sensor coupled or adjacent to the medication chamber, the mass sensor being in communication with the control sub-system, the mass sensor generating data indicative of a mass of medicinal fluid within the medication chamber.

12. The system of claim 11, wherein the control sub-system calculates a flow rate and/or volume of the medicinal fluid exiting the outlet of the medication chamber based on the data generated by the mass sensor.

13. The system of claim 1 further comprising a medication chamber pressure sensor coupled or adjacent to the medication chamber, the medication chamber pressure sensor being in communication with the control sub-system, the medication chamber pressure sensor generating data indicative of a volume of medicinal fluid within the medication chamber.

14. The system of claim 13, wherein the control sub-system calculates a flow rate and/or volume of the medicinal fluid exiting the outlet of the medication chamber based on the data generated by the medication chamber pressure sensor.

15. The system of claim 1, wherein the control sub-system further calculates occlusions within the fluid communication path using the first pressure value and the second pressure value.

16. The system of claim 1 further comprising:

a medication chamber pressure sensor coupled to or adjacent to the medication chamber, the medication chamber pressure sensor being in communication with the control sub-system and which generates a third pressure value characterizing a level of pressure within the medication chamber;

wherein the control sub-system calculates an amount of medicinal fluid within the medication chamber based on a differential pressure measurement using the first pressure value and the third pressure value.

17. The system of claim 1, wherein the electromechanical air pump is a piezoelectric air pump.

18. The system of claim 1 further comprising:

a bubble detection sensor coupled to or adjacent to the medication chamber, the bubble detection sensor being in communication with the control sub-system, the bubble detection sensor being configured to identify bubbles within the medicinal fluid.

19. The system of claim 18 further comprising:

a bubble elimination system coupled to or adjacent to the medication chamber, the bubble elimination system being in communication with the control sub-system, the bubble elimination system being configured to selectively remove bubbles within the medicinal fluid identified by the bubble detection sensor.

20. The system of claim 1 further comprising:

an occlusion detection sensor coupled to or adjacent to the medication chamber, the occlusion detection sensor being in communication with the control sub-system, the occlusion detection sensor being configured to identify an occlusion within the fluid communication path.

21. The system of claim 1 further comprising:

a user interface comprising a display and at least one input element configured to alter a parameter associated with delivery of the medicinal fluid to the patient.

22. The system of claim 1, wherein the handheld housing further encapsulates at least portion of the medication chamber.

23. The system of claim 1 further comprising:

a communications interface configured to bi-directionally exchange data over a communications network with a remote computing device associated with delivery of the medicinal fluid.

24. A system for delivering a medicinal fluid to a patient comprising:

a housing having a shape and size to receive and secure a detachable, pre-filled syringe, at least a portion of the syringe defining a medication chamber having a variable volume, the medication chamber configured to store medicinal fluid and having an outlet forming a fluid communication path to the patient;

a pressure delivery chamber having a variable volume and configured to store pressure controllably, the pressure delivery chamber being fluidically isolated from the medication chamber;

a movable delivery element disposed between the medication chamber and the pressure delivery chamber, the movable delivery element having a shape and size to fluidically isolate the medication chamber and the pressure delivery chamber;

a pressure source coupled to the pressure delivery chamber, the pressure source comprising an elastomeric device that is pressurized with an impelling fluid, the impelling fluid being isolated from the medicinal fluid, the pressure source being configured to be utilized multiple times to selectively increase or decrease pressure within the pressure delivery chamber;

a medication reservoir configured to be coupled to the medication chamber and configured to hold additional medicinal fluid; and a control sub-system configured to selectively send signals to cause pressure to be delivered from the pressure source to the pressure delivery chamber thereby causing the movable delivery element to apply pressure to the medicinal fluid in the medication chamber, the application of pressure to the medicinal fluid in the medication chamber causing the medicinal fluid to exit the medication chamber at the outlet along the fluid communication path to the patient, the control sub-system being further configured to automatically extract fluid from the medication reservoir and transfer the extracted fluid to the medication chamber.

25. A system for delivering a medicinal fluid to a patient comprising:

means for securing a detachable, pre-filled syringe, at least a portion of the syringe defining a medication chamber having a variable volume, the medication chamber configured to store medicinal fluid and having an outlet forming a fluid communication path to the patient;

a pressure delivery chamber having a variable volume and configured to store pressure controllably, the pressure delivery chamber being fluidically isolated from the medication chamber;

a movable delivery element disposed between the medication chamber and the pressure delivery chamber, the movable delivery element having a shape and size to fluidically isolate the medication chamber and the pressure delivery chamber;

a pressure source coupled to the pressure delivery chamber, the pressure source comprises a pneumatic pump configured to be utilized multiple times to selectively increase or decrease pressure within the pressure delivery chamber;

a control sub-system configured to selectively send signals to cause pressure to be delivered from the pressure source to the pressure delivery chamber thereby causing the movable delivery element to apply pressure to the medicinal fluid in the medication chamber, the application of pressure to the medicinal fluid in the medication chamber causing the medicinal fluid to exit the medication chamber at the outlet along the fluid communication path to the patient;

a medication reservoir configured to be coupled to the medication chamber and configured to hold additional medicinal fluid; and a handheld housing encapsulating each of the pressure delivery chamber, the movable delivery element, the pressure source, and the control sub-system;

the handheld housing being configured such that when the medication chamber is at or below a level of medicinal fluid, pressure applied from the pressure delivery chamber causes a suction effect when an opening between the medication reservoir and the medication chamber is open thereby drawing medicinal fluid from the medication reservoir into the medication chamber.

26. A system for delivering a medicinal fluid to a patient comprising:

a housing having a shape and size to be handheld and to receive and secure a detachable, pre-filled syringe without a plunger, the housing comprising a hinged lid to secure the pre-filled syringe, at least a portion of the syringe defining a medication chamber having a variable volume, the medication chamber configured to store medicinal fluid and having an outlet forming a fluid communication path to the patient;

a pressure delivery chamber having a variable volume and configured to store pressure controllably, the pressure delivery chamber being fluidically isolated from the medication chamber;

a movable delivery element within the housing and disposed between the medication chamber and the pressure delivery chamber, the movable delivery element having a shape and size to fluidically isolate the medication chamber and the pressure delivery chamber;

a pressure source self-contained within the housing and which is coupled to the pressure delivery chamber, the pressure source comprising an electromechanical air pump that is configured to be utilized multiple times to selectively increase or decrease pressure within the pressure delivery chamber;

a medication reservoir configured to be coupled to the medication chamber and configured to hold additional medicinal fluid;

a control sub-system configured to selectively send signals to cause pressure to be delivered from the pressure source to the pressure delivery chamber thereby causing the movable delivery element to apply pressure to the medicinal fluid in the medication chamber, the application of pressure to the medicinal fluid in the medication chamber causing the medicinal fluid to exit the medication chamber at the outlet along the fluid communication path to the patient;

a wireless communications interface configured to bidirectionally exchange data over a communications network with a remote computing device associated with delivery of the medicinal fluid including instructions to the control sub-system; and the housing encapsulating each of the pressure delivery chamber, the movable delivery element, the pressure source, the medication reservoir, the control sub-system, and the wireless communications interface.

27. A handheld system for delivering a medicinal fluid to a patient, comprising:

a housing sized and shaped to be held in one hand of a user while at least one input element is activated by another hand of the user, the housing comprising a hinged lid configured to open to receive a detachable, pre-filled syringe without an integral plunger and close to secure the detachable, pre-filled syringe, at least a portion of the syringe defining a medication chamber having a variable volume, the medication chamber configured to store medicinal fluid and having an outlet forming a fluid communication path to the patient;

a pressure delivery chamber having a variable volume and configured to store pressure controllably, the pressure delivery chamber being fluidically isolated from the medication chamber;

a movable delivery element within the housing and disposed between the medication chamber and the pressure delivery chamber, the movable delivery element comprising an elastomeric membrane or a bellows element with collapsible sides, the movable delivery element having a shape and a size to fluidically isolate the medication chamber and the pressure delivery chamber;

a pressure source self-contained within the housing and coupled to the pressure delivery chamber, the pressure source comprising a piezoelectric air pump configured to be utilized multiple times to selectively increase or decrease pressure within the pressure delivery chamber;

a valve manifold disposed between the pressure source and the pressure delivery chamber for selectively delivering pressure from the pressure source to the pressure delivery chamber at a controlled rate;

a pressure delivery chamber pressure sensor coupled to or adjacent to the pressure delivery chamber and configured to generate a first pressure value characterizing a level of pressure within the pressure delivery chamber;

a reference pressure chamber having a fixed volume and a reference pressure chamber pressure sensor coupled to or adjacent to the reference pressure chamber, the reference pressure chamber pressure sensor configured to generate a second pressure value characterizing a level of pressure within the reference pressure chamber;

a medication reservoir configured to be coupled to the medication chamber and configured to hold additional medicinal fluid;

a control sub-system configured to send signals to the piezoelectric air pump and the valve manifold to selectively cause pressure to be delivered from the pressure source to the pressure delivery chamber at the controlled rate, thereby causing the movable delivery element to deform and apply pressure to the medicinal fluid in the medication chamber, the application of pressure to the medicinal fluid causing the medicinal fluid to exit the medication chamber at the outlet along the fluid communication path to the patient, the control sub-system being configured to calculate an amount of medicinal fluid within the medication chamber based on a differential pressure measurement using the first pressure value and the second pressure value, and the control sub-system being further configured to calculate occlusions within the fluid communication path using the first pressure value and the second pressure value, the control sub-system being further configured to automatically extract fluid from the medication reservoir and transfer the extracted fluid to the medication chamber;

a user interface comprising an electronic display and at least one input element configured to alter a parameter associated with delivery of the medicinal fluid to the patient; and a wireless communications interface configured to bidirectionally exchange data over a communications network with a remote computing device associated with delivery of the medicinal fluid including instructions to the control sub-system;

the housing at least partially encapsulating each of the pressure delivery chamber, the movable delivery element, the pressure source, the valve manifold, the pressure delivery chamber pressure sensor, the reference pressure chamber, the reference pressure chamber pressure sensor, the medication reservoir, the control sub-system, and the wireless communications interface, the housing partially encapsulating the user interface such that the user interface remains accessible to the user.

28. The handheld system of claim 27, wherein the control sub-system is configured to generate signals that cause the pressure source in concert with the valve manifold to dispense medicinal fluid out of the medication chamber in a stepped manner to deliver a series of discrete medicinal fluid volumes.

29. The handheld system of claim 27, wherein the prefilled syringe is mechanically and fluidically coupled to the housing using a mechanical connector comprising a Luer lock.

30. The handheld system of claim 27, further comprising an alarm element in communication with the control sub-system, wherein the control sub-system is configured to cause the alarm element to convey a visual indicator or an audio signal associated with operation of the handheld system.

31. The handheld system of claim 27, wherein the wireless communications interface is configured to bi-directionally exchange data over a communications network with the remote computing device, the data comprising information associated with delivery of the medicinal fluid to the patient.

* * * * *